United States Patent [19]

Kardorff et al.

[11] Patent Number: 5,145,873
[45] Date of Patent: * Sep. 8, 1992

[54] SPECIFICALLY SUBSTITUTED CYCLOPROPANECARBOXAMIDES AND THEIR USE FOR CONTROLLING PESTS

[75] Inventors: Uwe Kardorff, Mannheim; Hans-Juergen Neubauer, Muenster-Hiltrup; Joachim Leyendecker, Ladenburg; Christoph Kuenast, Otterstadt; Peter Hofmeister, Neustadt; Wolfgang Krieg, Weingarten; Rainer Buerstinghaus, Telgte, all of Fed. Rep. of Germany

[73] Assignee: Basf Aktiengesellschaft, Ludwigshafen, Fed. Rep. of Germany

[*] Notice: The portion of the term of this patent subsequent to Aug. 22, 2006 has been disclaimed.

[21] Appl. No.: 435,670

[22] Filed: Nov. 14, 1989

[30] Foreign Application Priority Data

Dec. 9, 1988 [DE] Fed. Rep. of Germany ....... 3841433

[51] Int. Cl.$^5$ .................. A61K 31/165; C07C 233/60
[52] U.S. Cl. .................................... 514/624; 514/613; 564/123; 564/190
[58] Field of Search .................. 564/190; 514/624

[56] References Cited

U.S. PATENT DOCUMENTS

| 4,166,735 | 9/1979 | Pilgram et al. | 564/190 |
| 4,710,518 | 12/1987 | Kurahashi et al. | 564/190 |
| 4,859,706 | 8/1989 | Buerstinghaus et al. | 564/190 |

FOREIGN PATENT DOCUMENTS 0285934 10/1988 European Pat. Off. ............ 564/190

Primary Examiner—Glennon H. Hollrah
Assistant Examiner—S. Treanor
Attorney, Agent, or Firm—Keil & Weinkauf

[57] ABSTRACT

Cyclopropanecarboxyamides of the general formula I

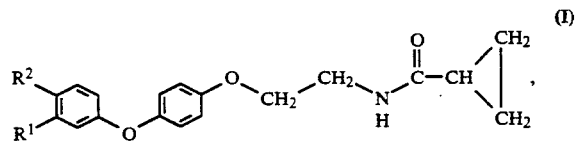

Where $R^1$ is $C_1$-$C_4$-alkyl, fluorine, chlorine, bromine, $C_1$-$C_3$-haloalkyl or $C_1$-$C_3$-haloalkoxy, $R^2$ is hydrogen, fluorine, chlorine or bromine, with the proviso that $R^1$ is not fluorine if $R^2$ is H, and pesticides containing these compounds.

10 Claims, No Drawings

SPECIFICALLY SUBSTITUTED CYCLOPROPANECARBOXAMIDES AND THEIR USE FOR CONTROLLING PESTS

The present invention relates to novel substituted cyclopropanecarboxamides of the general formula I

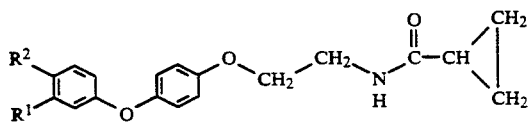

where $R^1$ is $C_1$–$C_4$-alkyl, fluorine, chlorine, bromine, $C_1$–$C_3$-haloalkyl or $C_1$–$C_3$-haloalkoxy and $R^2$ is hydrogen, fluorine, chlorine or bromine, with the proviso that $R^1$ is not fluorine if $R^2$ is H.

The present invention furthermore relates to pesticides which contain the compounds I and a method for controlling pests.

DE-A 3 628 082 discloses variously substituted cyclopropanecarboxamides of the structure A

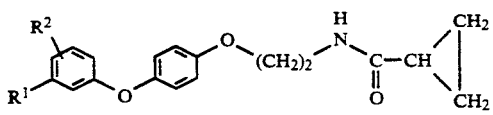

where $R^2$ is preferably in the 4-position and $R^1$ is hydrogen or, inter alia, halogen, $C_1$–$C_3$-alkyl or trifluoromethyl. In the case of disubstitution in the 4-phenoxy radical, which is described for halogen substituents, the combination 3,5-dihalo or 2,4-difluoro is stated.

It is an object of the present invention to provide novel cyclopropanecarboxamides which are superior in their action to known cyclopropanecarboxamides.

We have found that this object is achieved and that the specifically substituted cyclopropanecarboxamides of the formula I which are defined at the outset are very suitable for controlling pests.

In view of the compounds known from the prior art, it is surprising that substitution of the 4-phenoxy radical in the 3-position, if necessary a combination with halogen substitution in the 4-position, leads to cyclopropanecarboxamides having particularly advantageous properties (cf. Comparative Experiments A to D).

The cyclopropanecarboxamides I are prepared in a conventional manner from the 2-(4-phenoxyphenoxy)-ethylamines II

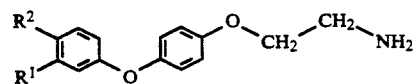

by reaction with the corresponding cyclopropanecarbonyl halides III

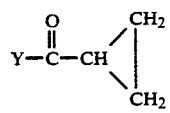

where Y is halogen, such as fluorine, chlorine or bromine, preferably chlorine, in the presence of an acid acceptor.

The acid acceptor used may be a 4-phenoxyphenoxyethylamine II, but conventional bases are usually used as acid acceptors, in particular aliphatic, aromatic or heterocyclic amines, eg. triethylamine, dimethylamine, diisopropylamine, piperidine, dimethylaniline, dimethylbenzylamine, pyridine and 4-dimethylaminopyridine; hydroxides of alkali metals and of alkaline earth metals, for example sodium hydroxide, potassium hydroxide and calcium hydroxide; alcoholates of alkali metals and of alkaline earth metals, for example sodium methylate, sodium ethylate, calcium methylate and potassium tertbutylate; alkali metal or alkaline earth metal hydrides, for example sodium hydride, potassium hydride or calcium hydride, and alkali metal or alkaline earth metal carbonates, for example sodium carbonate, potassium carbonate or calcium carbonate.

The ratio of acid acceptor to acyl halide III is not particularly critical and is in general from 0.1:1 to 20:1, preferably from 0.7:1 to 5:1, particularly preferably from 0.9:1 to 1.5:1.

The starting materials II and III are usually used in a stoichiometric ratio. An excess of one or other component may, however, be quite advantageous in specific cases.

The reaction usually takes place at an adequate rate at above $-30°$ C. In general, the temperature is from $-30°$ to $130°$ C., in particular from $-10°$ to $80°$ C. Since the reaction takes place with evolution of heat in some cases, it may be advantageous to provide a means of cooling.

The reaction is advantageously carried out in a solvent or diluent under atmospheric, superatmospheric or reduced pressure.

Suitable solvents or diluents are aliphatic or aromatic hydrocarbons or chlorohydrocarbons, for example petroleum ether, n-pentane, n-hexane, hexane isomer mixtures, benzene, toluene, xylene, gasoline, dichloromethane, chloroform, carbon tetrachloride, 1,2-dichloroethane and chlorobenzene; ethers and esters, such as diethyl and di-n-butyl ether, methyl tert-butyl ether, tetrahydrofuran, dioxane and ethyl acetate; ketones, such as acetone, methyl ethyl ketone and methyl isopropyl ketone; nitriles, such as acetonitrile and propionitrile; alcohols, such as methanol, ethanol, n-propanol and isopropanol, and aprotic dipolar solvents, such as dimethylformamide, dimethyl sulfoxide and pyridine. Mixtures of these substances may also be used as solvents and diluents.

Some of the 2-(4-phenoxyphenoxy)-ethylamines II required for the preparation of the compounds I are known from Houben-Weyl, Vol. VI, 3, Methoden der organischen Chemie, Thieme Verlag, 1965, 85 et seq., or can be prepared by the methods described there.

The acyl halides III also required are known, and the acyl chloride in particular is commercially available.

The novel compounds of the formula I may furthermore be prepared by virtually all known methods of carboxamide synthesis, for example by reacting 2-(4-phenoxyphenoxy)-ethylamines II with corresponding cyclopropanecarboxylic esters, cyclopropanecarboxylic acids and their salts, cyclopropanecarboxylic anhydrides or ketone derivatives (cf. Ferri, Reaktionen der organischen Synthese, Georg Thieme Verlag, Stuttgart, 1978, page 542, and the literature cited there).

Some of the novel compounds of the formula I are obtained in the form of colorless or slightly brownish oils, which can be freed from the last volatile components by prolonged heating under reduced pressure at moderately elevated temperatures (incipient distillation) and can be purified in this manner. If the compounds of the formula I are in crystalline form, they can be purified by recrystallization.

In formula I, $R^1$ is straight-chain or branched $C_1$–$C_4$-alkyl, such as methyl, ethyl, propyl, isopropyl, butyl, isobutyl, sec-butyl or tert-butyl, fluorine, chlorine or bromine, $C_1$–$C_3$-haloalkyl, preferably fluoro- or chloroalkyl, such as fluoromethyl, difluoromethyl, trifluoromethyl, pentafluoroethyl, 2,2,2-trifluoroethyl, trichloromethyl or 2,2,2-trichloroethyl, trifluoromethyl being particularly preferred, or $C_1$–$C_3$-haloalkoxy, preferably fluoro- or chloroalkoxy, such as trifluoromethoxy, 1,1,2,2-tetrafluoroethoxy, pentafluoroethoxy or trichloromethoxy, trifluoromethoxy and chloroalkoxy being particularly preferred, $R^2$ is hydrogen or fluorine, chlorine or bromine, in particular fluorine.

In contrast to most of the pesticides known to date, which act as contact or digested poisons and kill, incapacitate or expel the animals, the compounds of the formula I intervene in the hormone system of the animal organism. In the case of insects, for example, the transformation to the imago, the laying of viable eggs and the development of laid, normal eggs are disturbed and the sequence of generations is thus interrupted. The agents according to the invention are virtually completely nontoxic to vertebrates.

Most of the compounds of the formula I are furthermore readily degraded into substances which occur in nature and are further decomposed by microorganisms.

The novel compounds are also suitable for effectively combating pests from the class of insects, mites and nematodes. They may be used as pesticides in crop protection, and in the hygiene, stores protection and veterinary sectors.

Examples of injurious insects from the Lepidoptera order are *Agrotis ypsilon, Agrotis segetum, Alabama argillacea, Anticarsia gemmatalis, Argyresthia conjugella, Autographa gamma, Bupalus piniarius, Cacoecia murinana, Capua reticulana, Cheimatobia brumata, Choristoneura fumiferana; Choristoneura occidentalis, Cirphis unipuncta, Cydia pomonella, Dendrolimus pini, Diaphania nitidalis, Diatraea grandiosella, Earias insulana, Elasmopalpus lignosellus, Eupoecilia ambiguella, Evetria bouliana, Feltia subterranea, Galleria mellonella, Grapholita funebrana, Grapholita molesta, Heliothis armigera, Heliothis virescens, Heliothis zea, Hellula undalis, Hibernia defoliaria, Hyphantria cunea, Hyponomeuta malinellus, Keifferia lycopersicella, Lambdina fiscellaria, Laphygma exigua, Leucoptera coffeella, Leucoptera scitella, Lithocolletis blancardella, Lobesia botrana, Loxostege sticticalis, Lymantria dispar, Lymantria monacha, Lyonetia clerkella, Malacosoma neustria, Mamestra brassicae, Orgyia pseudotsugata, Ostrinia nubilalis, Panolis flamea, Pectinophora gossypiella, Peridroma saucia, Phalera bucephala, Phthorimaea operculella, Phyllocnistis citrella, Pieris brassicae, Plathypena scarbra, Plutella xylostella, Pseudoplusia includens, Phyacionia frustrana, Scrobipalpula absoluta, Sitotroga cerelella, Sparganothis pilleriana, Spodoptera frugiperda, Spodoptera littoralis, Spodoptera litura, Thaumatopoea pityocampa, Tortrix viridana, Trichoplusia ni* and *Zeiraphera canadensis.*

Examples from the Coleoptera order are *Agrilus sinuatus, Agriotes lineatus, Agriotes obscurus, Amphimallus solstitialis, Anisandrus dispar, Anthonomus grandis, Anthonomus pomorum, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcata, Ceuthorrhynchus assimilis, Ceuthorrynchus napi, Chaetocnema tibialis, Conoderus vespertinus, Crioceris asparagi, Diabrotica longicornis, Diabrotica* 12-punctata, Diabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Onlema oryzae, Ortiorrhynchus sulcatus, Ortiorrhynchus ovatus, Phaedon cochleariae, Phyllotreta chrysocephala, Phyllophaga sp., Phyllopertha horticola, Phyllotreta nemorum, Phyllotreta striolata, Popillia japonica, Sitona lineatus and *Sitophilus granaria.*

Examples from the Diptera order are *Aedes aegypti, Aedes vexans, Anastrepha ludens, Anopheles maculipennis, Ceratitis capitata, Chrysomya bezziana, Chrysomya hominivorax, Chrysomya macellaria, Contarinia sorghicola, Cordylobia anthropophaga, Culex pipiens, Dacus cucurbitae, Dacus oleae, Dasineura brassicae, Fannia canicularis, Gasterophilus intestinalis, Glossia morsitans, Haematobia irritans, Haplodiplosis equestris, Hylemyia platura, Hypoderma lineata, Liriomyza sativae, Liriomyza trifolii, Lucilia caprina, Lucilia cuprina, Lucilia sericata, Lycoria pectoralis, Mayetiola destructor, Musca domestica, Muscina stabulans, Oestrus ovis, Oscinella frit, Pegomya hysocyami, Phorbia antiqua, Phorbia brassicae, Phorbia coarctata, Rhagoletis cerasi, Rhagoletis pomonella, Tabanus bovinus, Tipula oleracea* and *Tipula paludosa.*

Examples from the Thysanoptera order are *Frankliniella fusca, Frankliniella occidentalis, Frankliniella tritici, Scirtothrips citri, Thrips oryzae, Thrips palmi* and *Thrips tabaci.*

Examples from the Hymenoptera order are *Athalia rosae, Atta cephalotes, Atta sexdens, Atta texana, Hoplocampa minuta, Hoplocampa testudinea, Monomorium pharaonis, Solenopsis geminata* and *Solenopsis invicta.*

Examples from the Heteroptera order are *Acrosternum hilare, Blissus leucopterus, Cyrtopeltis notatus, Dysdercus cingulatus, Dysdercus intermedius, Eurygaster integriceps, Euchistus impictiventris, Leptoglossus phyllopus, Lygus lineolaris, Lygus pratensis, Nezara viridula, Piesma quadrata, Solubea insularis* and *Thyanta perditor.*

Examples from the nematode class are root-knot nematodes, e.g., *Meloidogyne hapla, Meloidogyne incognita* and *Meloidogyne javanica,* cyst-forming nematodes, e.g., *Globodera rostochiensis, Heterodera avenae, Heterodera glycinae, Heterodera schachtii, Heterodera trifolii,* stem and leaf eelworms, e.g., *Belonolaimus longicaudatus, Ditylenchus destructor,* Ditylenchus dipsaci, Heliocotylenchus multicinctus, Longidorus elongatus, Radopholus similis, Rotylenchus robustus, Trichodorus primitivus, Tylenchorhynchus claytoni, Tylenchorhynchus dubius, Pratylenchus neglectus, Pratylenchus penetrans, Pratylenchus curvitatus, Pratylenchus goodeyi.

The active ingredients may be applied for instance as such, or in the form of formulations or application forms prepared therefrom, e.g., directly sprayable solutions, powders, suspensions, dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredients according to the invention as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Examples of formulations are given below.

I. 5 parts by weight of compound no. 1 is intimately mixed with 95 parts by weight of particulate kaolin. A dust is obtained containing 5% by weight of the active ingredient.

II. 30 parts by weight of compound no. 2 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

III. 10 parts by weight of compound no. 4 is dissolved in a mixture consisting of 90 parts by weight of xylene, 6 parts by weight of the adduct of 8 to 10 moles of ethylene oxide and 1 mole of oleci acid-N-monoethanolamide, 2 parts by weight of the calcium salt of dodecylbenzenesulfonic acid, and 2 parts by weight of the adduct of 40 moles of ethylene oxide and 1 mole of castor oil.

IV. 20 parts by weight of compound no. 3 is dissolved in a mixture consisting of 60 parts by weight of cyclohexanone, 30 parts by weight of isobutanol, 5 parts by weight of the adduct of 7 moles of ethylene oxide and 1 mole of isooctylphenol, and 5 parts by weight of the adduct of 40 moles of ethylene oxide and 1 mole of castor oil.

V. 80 parts by weight of compound no. 5 is well mixed with 3 parts by weight of the sodium salt of diisobutylnaphthalene-alpha-sulfonic acid, 10 parts by weight of the sodium salt of a lignin-sulfonic acid obtained from a sulfite waste liquor, and 7 parts by weight of powdered silica gel, and triturated in a hammer mill.

Granules, e.g., coated, impregnated or homogeneous granules, may be prepared by bonding the active ingredients to solid carriers. Examples of solid carriers are mineral earths such as silicic acid, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations generally contain from 0.1 to 95, and preferably 0.5 to 90, % by weight of active ingredient.

The active ingredient concentrations in the finished formulations may vary over a wide range. Generally, they are from 0.0001 to 10, and preferably from 0.01 to 1, %. The active ingredients may also successfully be used in the ultra-low-volume (ULV) method, where it is possible to apply formulations containing more than 95 wt % of active ingredient, or even the active ingredient without additives.

In the open, the amount of active ingredient applied is for example from 0.2 to 10, particularly from 0.5 to 2, kg/ha.

There may be added to the active ingredients (if desired, immediately before use (tankmix)) oils of various types, herbicides, fungicides, other pesticides and bactericides. These agents may be added to the active ingredients according to the invention in a weight ratio of from 1:10 to 10:1.

EXAMPLE 1

N-2-[4-(3-methylphenoxy)-phenoxy]-ethycyclopropane carboxamide

At room temperature, 2.0 g of cyclopropanecarboxylic acid chloride in 5.8 ml of dichloromethane is dripped into 4.3 g (17.7 mmol) of [4-(3-methylphenoxy)-phenoxy]-ethylamine in 17.5 ml of pyridine. After all has been dripped in, the mixture is stirred for 14 hours at room temperature. It is then poured into water and the organic phase is separated. The aqueous phase is extracted with dichloromethane and the combined organic phases are washed with water. Drying is followed by evaporating down under reduced pressure, and the residue is recrystallized from hexane/ethyl acetate. A white crystalline compound is obtained; m.p.: 114° C.

Yield: 4.5 g; 82% of theory $C_{19}H_{21}NO_3$

Calc.: C 73.29%, H 6.80%, N 4.50%, Found: C 72.3%, H 6.8%, N 4.5%.

Infrared absorptions [cm$^{-1}$]: 1502, 1484, 1461, 1262, 1241, 1206, 1057.

Compounds I listed in the following table may be obtained analogously to this example:

$$R^2 \diagdown \diagup O \diagdown CH_2 \diagdown CH_2 \diagdown N \diagdown \underset{H}{C} \diagdown CH \diagup \overset{CH_2}{\underset{CH_2}{}} \quad (I)$$

| Example | R$^1$ | R$^2$ | M.p. (°C.) |
|---|---|---|---|
| 2 | Cl | H | 87–90 |
| 3 | Br | H | 88–90 |
| 4 | F$_3$C | H | 67–68 |
| 5 | C$_2$H$_5$ | H | 84 |
| 6 | OCF$_3$ | H | 85–88 |
| 7 | Cl | F | 55–57 |
| 8 | F | F | 67 |

USE EXAMPLES

In the following examples, the action of compounds according to the invention, or agents containing them, on pests was compared with that of compounds disclosed in EP-A 258,733 (German application P 36 28 082). The purity of the substances and of the comparative agents was >95%.

The concentrations at which the investigated compounds achieve 100% or 80% kill or inhibition are the minimum concentrations (action threshold). At least two experiments were carried out for each concentration and an average was formed.

The formulation employed was a 10% emulsion concentrate containing 70 wt % of cyclohexanone, 20 wt % of Nekanil LN ® (=Lutensol AP6, a wetting agent having an emulsifying and dispersing action and based on ethoxylated alkylphenols), Emulphor EL ® (=Emulan EL ®, an emulsifier based on ethoxylated fatty alcohols) and 10% of active ingredient. The concentrations given in the examples were obtained by diluting the formulated active ingredient with water.

EXAMPLE A

Dysdercus intermedius (Cotton Stainer); Ovicidal Action

Pieces of adhesive tape (about 0.8 cm) were stuck to the top edge of plastic plant markers. 24 hours before commencement of the experiment, eggs of the cotton stainer contained in a vessel were attached to the adhesive strips by dipping the markers into the vessel.

The eggs were then dipped for about 5 seconds into aqueous formulations of the active ingredients and excess liquid was allowed to drip off onto a filter paper, care being taken to prevent the eggs coming into contact with the paper.

The markers were placed (adhesive tape up) in plastic pallets. Half a roll of absorbent cotton was moistened with water and placed in each beaker to prevent drying out, and the pallets were covered with a glass plate.

Assessment took place after about 8 days (after the larvae in the control batch had hatched). Hatch inhibition was assessed in %. The results are given in Table A.

TABLE A

| Compound No. | Substitution at 4-phenoxy radical | Active ingredient conc. (ppm) | Inhibition (%) |
|---|---|---|---|
| 8 | 3,4-F$_2$ | 0.4 | 80 |
| 19* | 2,4-F$_2$ | 400 | 80 |
|  |  | 0.4 | 0 |

*from EP-A 258, 733

EXAMPLE B

Dysdercus intermedius (Cotton Stainer); Breeding Experiment

The experiment was carried out in 1 liter jars containing 200 g of sterile quartz sand (particle size 0–3 mm). Prior to the experiment, 20 ml of the aqueous active ingredient formulations was poured onto this sand. Ten larvae of the fourth stage were then introduced into each jar. The food proffered was swollen cottonseed, which was changed once a week. The sand was also moistened once a week with pure water. The temperature was kept at 25° to 27° C. The observation period extended to molting to the adult. A sample was considered to be effective when, at the end of the experiment, the animals were either dead or exhibited considerable morphological defects, or giant larvae or adultoids had formed (i.e., were not viable-designated as mortality in Table B).

The results are given in Table B.

TABLE B

| Compound No. | Substitution at 4-phenoxy radical | Active ingredient conc. (ppm) | Mortality (%) |
|---|---|---|---|
| 1 | 3-CH$_3$ | 1 | 100 |
| 22* | 4-CH$_3$ | 20 | ineffective |
| 3 | 3-Br | 0.04 | 100 |
| 27* | 4-Br | 10 | ineffective |

*from EP-A 258, 733

EXAMPLE C

Breeding Experiment with Aedes aegypti

At 25° C., formulations of the active ingredients were added to 200 ml of tapwater in 250 ml plastic beakers. Subsequently, 20 to 30 mosquito larvae in the 3rd to 4th larval stage were then introduced. During the experiment the larvae were fed once with a powdered commercially available fishfood (Tetramin ®). The mortality was assessed after 10 to 12 days.

The results are given in Table C.

TABLE C

| Compound No. | Substitution at 4-phenoxy radical | Active ingredient conc. (ppm) | Mortality (%) |
|---|---|---|---|
| 2 | 3-Cl | 0.0002 | 100 |
| 3 | 3-Br | 0.1 | 100 |
| 17* | 3-F | 0.1 | ineffective |
| 15* | 4-Cl | 0.02 | 100 |
|  |  | 0.0002 | ineffective |

*from EP-A 258, 733

EXAMPLE D

Breeding Experiment with Prodenia litura

Breeding took place in 100 ml plastic beakers containing about 50 ml of a standard nutrient culture medium to which the active ingredients had been carefully admixed while in the liquid state. For each concentration, one beaker containing 5 caterpillars of the fourth larval stage was used. The temperature was kept at 25° to 26° C. The beakers were monitored until the moths emerged. The sample was considered to be effective when huge larvae were produced.

The results are given in Table D.

TABLE D

| Compound No. | Substitution at 4-phenoxy radical | Active ingredient conc. (ppm) | Mortality (%) |
|---|---|---|---|
| 4 | 3-$CF_3$ | 0.0002 | 100 |
| 1 | 3-$CH_3$ | 0.2 | 100 |
| 22* | 4-$CH_3$ | 1 | ineffective |
| 2 | 3-Cl | 0.02 | 100 |
| 3 | 3-Br | 0.001 | 100 |
| 17* | 3-F | 0.002 | 100 |
| 15* | 4-Cl | 0.1 | 100 |
| 27* | 4-Br | 0.4 | 100 |
|  |  | 0.001 | ineffective |
| 8 | 3,4-$F_2$ | 0.004 | 100 |
| 9 | 2,4-$F_2$ | 0.02 | 100 |

*from EP-A 258, 733

We claim:

1. A substituted cyclopropanecarboxamide of the formula I $$R^2\text{-}\underset{R^1}{\bigcirc}\text{-}O\text{-}\bigcirc\text{-}O\text{-}CH_2\text{-}CH_2\text{-}\underset{H}{N}\text{-}\underset{\|}{\overset{O}{C}}\text{-}CH\overset{CH_2}{\underset{CH_2}{\diagup\!\!\!\diagdown}} \quad (I)$$

where $R^1$ is fluorine, chlorine, bromine and $C_1$-$C_3$-haloalkyl, $R^2$ is hydrogen, fluorine, chlorine or bromine, with the proviso that $R^1$ is not fluorine if $R^2$ is H.

2. A substituted cyclopropanecarboxamide of the formula I as set forth in claim 1, where $R^1$ is chlorine, bromine, trifluoromethyl or trifluoromethoxy and $R^2$ is hydrogen.

3. A substituted cyclopropanecarboxamide of the general formula I as set forth in claim 1, where $R^1$ is fluorine, chlorine or bromine and $R^2$ is fluorine.

4. An insecticidal, miticidal and nematodicidal composition comprising an effective amount of a cyclopropanecarboxamide of the formula I as set forth in claim 1 and solid or liquid carriers.

5. An insecticidal, miticidal and nematodicidal at composition as set forth in claim 4, containing from 0.01 to 95 wt % of a cyclopropanecarboxamide of the formula I.

6. A process for the control of insects, mites and nematodes, wherein an effective amount of a cyclopropanecarboxamide of the formula I as set forth in claim 1 is allowed to act on the pests or their habitat.

7. A substituted cyclopropanecarboxamide of the formula I as set forth in claim 1, wherein $R^1$ is chlorine and $R^2$ is hydrogen.

8. A substituted cyclopropanecarboxamide of the formula I as set forth in claim 1, wherein $R^1$ is bromine and $R^2$ is hydrogen.

9. A substituted cyclopropanecarboxamide of the formula I as set forth in claim 1, wherein $R^1$ is $CF_3$ and $R^2$ is hydrogen.

10. A substituted cyclopropanecarboxamide of the formula I as set forth in claim 1, wherein $R^1$ is fluorine and $R^2$ is fluorine.

* * * * *